United States Patent [19]
Behl et al.

[11] Patent Number: 5,580,574
[45] Date of Patent: Dec. 3, 1996

[54] PHARMACEUTICAL COMPOSITION FOR TRANSDERMAL DELIVERY

[75] Inventors: Charanjit R. Behl, Nutley, N.J.; Peter Hofmann, Weil-Haltingen, Germany

[73] Assignee: Hoffmann-La Roche Inc., Nutley, N.J.

[21] Appl. No.: 234,214

[22] Filed: Apr. 28, 1994

[51] Int. Cl.$^6$ .............. A61K 9/70; A61F 13/00; A61L 15/10

[52] U.S. Cl. .......... 424/449; 514/784; 514/785; 514/786; 514/946; 514/947; 514/969

[58] Field of Search ............................. 424/449

[56] References Cited

U.S. PATENT DOCUMENTS

| | | | |
|---|---|---|---|
| 4,537,776 | 8/1985 | Cooper I | 514/424 |
| 4,557,934 | 12/1985 | Cooper II | 424/128 |
| 4,626,539 | 12/1986 | Aungst et al. | 514/282 |
| 4,719,239 | 1/1988 | Muller et al. | 514/785 |
| 4,722,941 | 2/1988 | Eckert et al. | 514/784 |
| 4,789,547 | 12/1988 | Song et al. | 424/449 |
| 4,837,025 | 6/1989 | Guillemet et al. | 424/448 |
| 4,863,970 | 9/1989 | Patel et al. | 514/784 |
| 4,879,297 | 11/1989 | Mahjour et al. | 514/282 |
| 4,885,174 | 12/1989 | Bodor et al. | 424/449 |
| 4,959,365 | 9/1990 | Francoeur et al. | 574/237.5 |
| 5,023,085 | 6/1991 | Francoeur et al. | 424/449 |
| 5,069,909 | 12/1991 | Sharma et al. | 424/449 |
| 5,096,715 | 3/1992 | Sinclair | 424/449 |
| 5,176,916 | 1/1993 | Yamanaka et al. | 424/448 |
| 5,196,410 | 3/1993 | Francoeur et al. | 514/159 |
| 5,212,199 | 5/1993 | Heiber et al. | 514/415 |
| 5,230,897 | 7/1993 | Griffin et al. | 424/449 |
| 5,234,957 | 8/1993 | Mantelle I | 514/772.6 |
| 5,238,933 | 8/1993 | Catz et al. | 514/236.2 |
| 5,296,222 | 3/1994 | Petersen et al. | 424/94.63 |
| 5,318,960 | 6/1994 | Toppo | 514/159 |
| 5,332,576 | 7/1994 | Mantelle II | 424/443 |
| 5,352,457 | 10/1994 | Jenkins | 424/448 |
| 5,362,497 | 11/1994 | Yamada et al. | 424/449 |
| 5,374,645 | 12/1994 | Kurihara-Bergstrom et al. | 514/882 |
| 5,378,473 | 1/1995 | Sharma et al. | 424/449 |

FOREIGN PATENT DOCUMENTS 0159167  4/1985  European Pat. Off. .

OTHER PUBLICATIONS

Ogiso, et al., Percutaneous Absorption of Clonazepam in Rabbit, Chem. Pharm. Bull. 37(2), pp. 442–445 (1989).

Ogiso, et al. Membrane–Controlled Transdermal Therapeutic System Containing Clonazepam and Anticonvulsant Activity After Its Application, Chem. Pharm. Bull. 37(2) pp. 446–449 (1989).

Kumar, et al., In Vitro Transdermal Delivery of $^{14}$C–Clonazepam Across Hairless Guinea Pig, Pharmaceutical Research, vol. 8, No. 10, Oct. 1991 (Supplement p. S–205).

Primary Examiner—Shep K. Rose
Attorney, Agent, or Firm—George W. Johnston; Ellen Ciambrone Coletti

[57] ABSTRACT

A pharmaceutical composition for transdermal delivery comprising an effective amount of an active ingredient selected from a benzodiazepine and a benzodiazepine antagonist; isopropanol; propylene glycol; oleic acid; and water. Additionally, the composition may contain diacetin, Cetiol B®, caprylic acid, Silicon fluid, Miglyol® 840 or transcutol.

27 Claims, No Drawings

PHARMACEUTICAL COMPOSITION FOR TRANSDERMAL DELIVERY

BACKGROUND OF THE INVENTION

Benzodiazepines are used as sedative hypnotics, in the treatment of anxiety disorders and in the treatment of seizures.

Benzodiazepine antagonists, such as, flumazenil, are used for a complete or partial reversal of the sedative effects of benzodiazepines and for the management of benzodiazepine overdose.

Benzodiazepines and benzodiazepine antagonists, are administered either via gastrointestinal tract or parenterally. Alternatively, a transdermanl route of drug delivery can be used. Generally, the most critical problem in this route is the lack of adequate absorption of drugs through the skin. Some chemical substances can improve this absorption and are called absorption enhancers. Previous studies involving a transdermal delivery system of benzodiazepines include the use of an ointment formulation containing the absorption enhancers Azone® and sorbitan monoleate, see, Ogiso, et al, *Percutaneous Absorption of Clonazepam in Rabbit*, Chem. Pharm. Bull. 37(2), pgs. 442–445 (1989); Ogiso, et al, *Membrane-Controlled Transdermal Therapeutic System Containing Clonazepam and Anticonvulsant Activity After Its Application*, Chem. Pharm. Bull. 37(2) pgs. 446–449 (1989) and an alcohol based formulation, see, Kumar et al. In Vitro Transdermal Delivery of $^{14}$C-Clonazepam Across Hairless Guinea Pig, Pharmaceutical Research, Volume 8, No. 10, October 1991 (Supplement) p. S-205.

SUMMARY OF THE INVENTION

The present invention relates to a pharmaceutical composition for transdermal delivery comprising an effective amount of an active ingredient selected from a benzodiazepine and benzodiazepine antagonist; propylene glycol; isopropanol; oleic acid; and water.

DETAILED DESCRIPTION OF THE INVENTION

The present invention relates to a pharmaceutical composition for transdermal delivery comprising an effective amount of an active ingredient selected from a benzodiazepine and benzodiazepine antagonist; isopropanol; propylene glycol; oleic acid; and water with or without an inert carrier.

As used herein, the term benzodiazepine means any active pharmaceutical compound in the benzodiazepine family, such as, diazepam, chlordiazepoxide, fluazepam, lorazepam and clonazepam, preferably clonazepam.

As used herein the term benzodiazepine antagonist means any compound antagonistic to benzodiazepines, such as, preferably flumazenil.

Preferably, isopropanol is present in the composition of the invention in the range of from about 10 to about 95 percent by weight of the composition. In a particularly preferred embodiment, isopropanol is present in the composition in an amount of about 20% by weight of the composition.

Preferably, propylene glycol is present in the composition of the invention in the range of from about 30 to about 50 percent by weight of the composition, particularly preferred in the range of from about 35 to about 45 percent by weight.

Preferably, oleic acid is present in the composition in the range of from about 1 to about 10 percent by weight of the composition, particularly preferred is about 5 percent by weight.

Preferably, water is present in the composition in the range of from about 10 to about 30 percent by weight of the composition, particularly preferred in the range of from about 20 to about 25 percent by weight.

When the active ingredient is a benzodiazepine antagonist such as flumazenil, preferably isopropanol is present in the composition in an amount of about 20 percent by weight of the composition; propylene glycol is present in the composition in an amount of from about 38 to about 47 percent by weight of the composition; oleic acid is present in the composition in an amount of about 5 percent by weight of the composition; and water is present in an amount of about 20 percent by weight of the composition.

The described pharmaceutical composition may contain additional enhancing materials such as, for example, Diacetin (glycerol diacetate from Davos Chemical), preferably in the range of from 5 to 15 percent by weight of the composition, particularly preferred in about 10 percent; Cetiol B® (dibutyl adipate from Henkel Co.), preferably in the range of from 1 to 10 percent by weight of the composition, particularly preferred in about 5 percent; caprylic acid, preferably in the range of from 1 to 10 percent of the composition, particularly preferred in about 5 percent; silicon fluid such as, Silicon Dow® 556 (polyphenyl methyl siloxane), preferably in the range of from 5 to 15 percent by weight of the composition, particularly preferred in about 10 percent; caprylic/capric triglyceride, such as Miglyol® 840 (propylene glycol diesters of saturated vegetable fatty acids of the chain lengths $C_8$–$C_{10}$, particularly 2% max caproic acid ($C_{6:0}$), 65–80% caprylic acid ($C_{8:0}$), 15–30% capric acid ($C_{10:0}$), and 3% max. linoleic acid ($C_{18:2}$) Dynamit Nobel) preferably in the range of from 5 to 15 percent by weight of the composition, particularly preferred in about 10 percent; transcutol (diethylene glycol monoethyl ether from Gattefosse), preferably in the range of from 5 to 15 percent by weight of the composition, particularly preferred in about 10 percent.

Pharmaceutical compositions in accordance with this invention can also be formulated to additionally contain conventional additives or supplementary ingredients in the usual amounts for such materials. The composition can be in the form of a gel, as well as in the form of a solution, preferably a thickened solution. By way of illustration, such additives or supplements include the following.

The gelling agents which can be used include, for example, hydroxymethyl cellulose, preferably in the range of from about 1 to 4 percent by weight of the composition; tragacanth, preferably in the range of from about 2 to 5 percent by weight of the composition; sodium alginate, preferably in the range of from about 2 to 10 percent by weight of the composition; gelatin, preferably in the range of from about 2 to 15 percent by weight of the composition; methylcellulose, preferably in the range of from about 2 to 4 percent by weight of the composition; sodium carboxymethylcellulose, preferably in the range of from about 2 to 5 percent by weight of the composition; and polyvinyl alcohols, preferably in the range of from about 10 to 20 percent by weight of the composition. A particularly preferred gelling agent is Klucel® HF (hydroxypropyl cellulose Hercules Inc., 1976) with a molecular weight in the 1,000,000 range and moisture content of 17% for 1,500–2,500, preferably present in the composition in the range of from about 1 to 4 percent by weight of the composition, particularly preferred in the range of from about 1 to 3 percent by weight of the composition. A sufficient amount of a particular gelling agent is added to obtain a desired consistency of the gel.

The preservatives which can be used in the invention include, for example, parabens, preferably at about 0.2 percent by weight of the composition; benzoic acid, preferably at about 0.2 percent by weight of the composition; and, chlorocresol, preferably at about 0.1 percent by weight of the composition.

If needed, antioxidants can be used in the gel formulations to improve the stability of the drug. These antioxidants include, for example, ascorbic palmitate, butylated hydroxyanisole, butylated hydroxytoluene, potassium sorbate, sodium bisulfate, sorbic acid, propyl gallate and sodium metabisulfite.

Preferably, the pharmaceutical composition of the invention is administered to a host in need of such treatment in a transdermal patch of a reservoir type.

Adhesives used in making transdermal patches for use with the invention include, for example, preferably polyisobutylene, silicone based adhesives and acrylic polymers. The adhesive polymers can be mixed with other excipients such as mineral oil to make them more suitable for a given purpose.

The backing membrane of a transdermal patch constitutes the upper part (exposed to the environment) of a transdermal patch and is made of materials such as, for example, preferably polyester films, ethyl vinyl acetate, polypropylene, polyethylene and polyvinyl-chloride.

A rate controlling membrane of a transdermal patch is placed in contact with the pharmaceutical composition of the invention and its other side is in contact with the skin of a host. The rate controlling membrane is made of materials such as, for example, preferably dimethylpolysiloxane, polyacetate, polyurethane and ethylene-vinyl acetate copolymer and polypropylene.

At the bottom of a transdermal patch, a protective liner is placed in contact with the adhesive layer. This liner protects against the drug release from the formulation reservoir until the liner is peeled off the patch and applied on the skin surface of the host. Such liners are made of materials including preferably polyethylene terephthalate film, polyester membrane and polycarbonate film.

Alternatively, one can make transdermal patches which are called monolithic or adhesive type patches. In this case, the drug is dispersed either in a suitable adhesive or in a suitable non-adhesive polymer and then the mixture is layered onto a membrane. A protective membrane is placed on the adhesive.

In vivo tests were utilized to evaluate the absorption of benzodiazepines and benzodiazepine antagonists administered in accordance with this invention.

Methods

General Procedure: Hairless guinea pigs (HGP) were anesthetized by using Ketamin-HCl and promazine. The side sites of the animals were cleaned with water. Zero time blood samples were withdrawn from the ocular site. The transdermal drug delivery systems were placed on the skin, two per animal providing a total area of 9.0 to 10.0 sq. cm., precisely measured. The animals were allowed to come out of anesthesia in between blood samples. Blood samples were withdrawn at 1.0, 2.0, 3.0, 4.0, and 6.0 hours. The blood was allowed to clot and then centrifuged to obtain serum. The drug concentration was determined by using an HPLC method. After the last sample point, the transdermal drug delivery system was removed from the animal's skin and the site was examined for any "obvious" signs of irritation/reddening.

Serum Collection

The animals were bled from the eye into Microtainer serum separator tubes (Becton Dickinson, 5960). The blood (0.6 mL) was centrifuged at 4,000 rpm for 15 minutes (4,400 g) on a Beckman J-6M centrifuge with a JS-4.2 rotor. Serum was separated and frozen until the HPLC analysis. Before sample preparation, the serum was thawed and centrifuged again.

Sample Preparation

Two hundred and fifty microliters of serum were mixed with 250 mcL of water and 25 mcL of an internal standard, flunitrazepam 1 mcg/mL in methanol, were added. The sample was purified on a solid phase mini column, Adsorbex RP-18 (100 mg; EM Science) using the sample preparation unit Adsorbex SPU). The columns were treated before with 2 mL of methanol and washed with 4 mL of water. Samples were applied and the columns were washed with 4 mL of water. The columns were dried under vacuum (5" Hg) and eluted with two portions of 125 mcL each of aceto-nitrile-:water (1:1).

HPLC Conditions

Samples were analyzed on a Waters HPLC system using Waters 600E controller, Waters 712 WISP automatic sample injector and Applied Biosystems 785A programmable absorbance detector.

| Column: | Waters Nova Pak C18, 75 × 3.9 mm |
|---|---|
| Flow rate: | 2.0 mL/min |
| Mobile Phase: | 25% acetonitrile in water (v/v) |
| Wavelength: | 310 nm |
| Data collection: | 2 points/sec, 1 V/AU, A/D = 0.1, rise time = 1 sec |
| Injection volume: | 100 mcL |
| Run time: | 15 min/sample |

The retention times of the inernal standard, flunitrazepam, and clonazepam or flumazenil were 5.5 and 4.5 minutes, respectively. The HPLC system is connected to a computer where a program was used to determine the area under the curve of the drug and the internal standard.

Lack Of Interference

The chromatogram of the HGP serum shows no peak at the retention time of clonazepam indicating an interference free detection of the drug.

Sensitivity And Linearity Of Response

A standard curve was made by adding flumazenil and the internal standard to HGP serum. A linear relationship was observed between the observed response and concentration of clonazepam in the range of 5 to 500 ng/mL. The recovery of the drug in these experiments was 75±15%, and was corrected using the internal standard. Apparent limit of quantification was found to be 5 ng/mL of flumazenil in the HGP serum.

Data Analysis

The HPLC data were computed in terms of drug concentration per unit volume of the serum and were plotted as a function of time. In such experiments, the blood levels are expected to rise to a maximum and then decline due to a decrease in the chemical potential of the drug in the patch.

No rate controlling membrane was placed at the bottom of the contemporary transdermal delivery dosage system.

| Formulation[a] | Results Max Blood Level Observed in HPG (ng/ml) |
|---|---|
| Example 1 | 762 |
| Example 2 | 733 |
| Example 3 | 753 |
| Example 4 | 200 |
| Example 5 | 377 |
| Example 6 | 249 |
| Example 7 | 530 |
| Control A[b] | 15 |

[a]Drug concentration was 10 mg/Gm; Dose was 12 mg per animal applied to an area of 9 cm sq.
[b]Control A contained 12 mg of flumazenil in a formulation comprised of 97% ethanol and 3% Klucel HF By way of illustration, some suitable pharmaceutical compositions in accordance with this invention are set forth below. While flumazenil, the preferred benzodiazepine antagonist for this invention, is used to illustrate the compositions, it should be understood that benzodiazepines and other benzodiazepine antagonists may be substituted in appropriate amounts.

EXAMPLE 1

| Flumazenil | 0.010 Gm |
|---|---|
| Isopropanol | 0.205 Gm |
| Propylene Glycol | 0.410 Gm |
| Oleic Acid | 0.050 Gm |
| Water | 0.205 Gm |
| Klucel BF | 0.010 Gm |
| Diacetin | 0.110 Gm |
| Total | 1.000 Gm |

EXAMPLE 2

| Flumazenil | 0.010 Gm |
|---|---|
| Isopropanol | 0.200 Gm |
| Propylene Glycol | 0.380 Gm |
| Water | 0.200 Gm |
| Oleic Acid | 0.050 Gm |
| Klucel HF | 0.010 Gm |
| Diacetin | 0.100 Gm |
| Cetiol B | 0.050 Gm |
| Total | 1.000 Gm |

EXAMPLE 3

| Flumazenil | 0.010 Gm |
|---|---|
| Isopropanol | 0.220 Gm |
| Propylene Glycol | 0.440 Gm |
| Water | 0.220 Gm |
| Caprylic Acid | 0.050 Gm |
| Oleic Acid | 0.050 Gm |
| Klucel HF | 0.010 Gm |
| Total | 1.000 Gm |

EXAMPLE 4

| Flumazenil | 0.010 Gm |
|---|---|
| Isopropanol | 0.198 Gm |
| Propylene Glycol | 0.426 Gm |
| Water | 0.198 Gm |
| Silicon Dow 556 | 0.099 Gm |
| Oleic Acid | 0.049 Gm |
| Klucel HF | 0.020 Gm |
| Total | 1.000 Gm |

EXAMPLE 5

| Flumazenil | 0.010 Gm |
|---|---|
| Isopropanol | 0.228 Gm |
| Propylene Glycol | 0.465 Gm |
| Water | 0.228 Gm |
| Oleic Acid | 0.049 Gm |
| Klucel HF | 0.020 Gm |
| Total | 1.000 Gm |

EXAMPLE 6

| Flumazenil | 0.010 Gm |
|---|---|
| Isopropanol | 0.198 Gm |
| Propylene Glycol | 0.426 Gm |
| Water | 0.198 Gm |
| Miglyol 840 | 0.099 Gm |
| Oleic Acid | 0.049 Gm |
| Klucel HF | 0.020 Gm |
| Total | 1.000 Gm |

EXAMPLE 7

| Flumazenil | 0.010 Gm |
|---|---|
| Isopropanol | 0.198 Gm |
| Propylene Glycol | 0.426 Gm |
| Water | 0.198 Gm |
| Oleic Acid | 0.049 Gm |
| Transcutol | 0.099 Gm |
| Klucel HF | 0.020 Gm |
| Total | 1.000 Gm |

The various ingredients of the formulations were mixed together in a glass apparatus. The drug was dissolved in this mixture. The gelling agent was added to this solution and the contents were mixed by using shear provided by a magnetic stirrer.

We claim:

1. A pharmaceutical composition for transdermal delivery consisting essentially of an effective transdermal amount of an active ingredient selected from a benzodiazepine and a benzodiazepine antagonist and as the essential transdermal absorption enhancers isopropanol; propylene glycol; oleic acid; and water.

2. The composition of claim 1, wherein the isopropanol is present in an amount of from about 10 to about 95 percent by weight of the composition, the propylene glycol is present in an amount of from about 30 to about 50 percent by weight of the composition, the oleic acid is present in an amount of from about 1 to about 10 percent by weight of the composition, and the water is present in an amount from about 10 to about 30 percent by weight of the composition.

3. The composition of claim 1, wherein the benzodiazepine is diazepam, lorazepam or clonazepam.

4. The composition of claim 2, wherein the benzodiazepine is clonazepam.

5. The composition of claim 1, wherein the benzodiazepine antagonist is flumazenil.

6. The composition of claim 5, wherein the isopropanol is present in an amount of from about 10.0 to about 95.0 percent by weight of the composition; the propylene glycol is present in an amount of from about 30 to about 50 percent by weight of the composition; the oleic acid is present in an amount of from about 1 to about 10 percent by weight of the composition, and water is present in an amount of from about 10 to about 30 percent by weight of the composition.

7. The composition of claim 6, wherein isopropanol is present in an amount of about 20 percent by weight of the composition; propylene glycol is present in an amount of from about 38 to about 47 percent by weight of the composition; oliec acid is present in an amount of about 5 percent by weight of the composition; and, water is present in an amount of about 20 percent by weight of the composition.

8. The composition of claim 6, further comprising hydroxypropyl cellulose in an amount of from about 1 to about 4 percent by weight of the composition.

9. The composition of claim 8, further comprising glycerol diacetate.

10. The composition of claim 9, wherein the glycerol diacetate is present in an amount of about 5 to about 15 percent by weight of the composition.

11. The composition of claim 10, wherein the glycerol diacetate is present in about 10 percent by weight of the composition.

12. The composition of claim 9, further comprising dibutyl adipate.

13. The composition of claim 12, wherein the dibutyl adipate is present in an amount of about 1 to about 10 percent by weight of the composition.

14. The composition of claim 13, wherein the dibutyl adipate is present in an amount of about 5 percent by weight of the composition.

15. The composition of claim 8, further comprising caprylic acid.

16. The composition of claim 15, wherein the caprylic acid is present in an amount of from about 1 to about 10 percent by weight of the composition.

17. The composition of claim 16, wherein the caprylic acid is present in about 5 percent by weight of the composition.

18. The composition of claim 13, further comprising silicon fluid.

19. The composition of claim 18, wherein the silicon fluid is present in an amount of about 5 to about 15 percent by weight of the composition.

20. The composition of claim 19, wherein the silicon fluid is present in about 10 percent by weight of the composition.

21. The composition of claim 8, further comprising caprylic/capric triglyceride.

22. The composition of claim 21, wherein the caprylic/capric triglyceride is present in an amount of from about 5 to about 15 percent by weight of the composition.

23. The composition of claim 22, wherein the caprylic/capric triglyceride is present in an amount of about 10 percent by weight.

24. The composition of claim 8, further comprising transcutol.

25. The composition of claim 24, wherein the transcutol is present in an amount of from about 5 to about 15 percent by weight of the composition.

26. The composition of claim 25, wherein the transcutol is present in an amount of about 10 percent by weight of the composition.

27. A pharmaceutical composition for transdermal delivery comprising an effective amount of flumazenil, isopropanol, propylene glycol, oleic acid, water, caprylic acid and hydroxypropyl cellulose.

\* \* \* \* \*

UNITED STATES PATENT AND TRADEMARK OFFICE
CERTIFICATE OF CORRECTION

PATENT NO. : 5,580,574
DATED : December 3, 1996
INVENTOR(S) : Behl, et al.

It is certified that error appears in the above-indentified patent and that said Letters Patent is hereby corrected as shown below:

IN THE CLAIMS

- Claim 1, Column 6, line 54: "A pharmaccutical composition" should read --- A pharmaceutical composition --- .

Signed and Sealed this

First Day of April, 1997

Attest:

BRUCE LEHMAN

Attesting Officer

Commissioner of Patents and Trademarks